US007303879B2

(12) United States Patent
Liu et al.

(10) Patent No.: US 7,303,879 B2
(45) Date of Patent: Dec. 4, 2007

(54) DETERMINATION OF SNP ALLELIC FREQUENCIES USING TEMPERATURE GRADIENT ELECTROPHORESIS

(75) Inventors: Zhaowei Liu, State College, PA (US); Yiqiong Wu, State College, PA (US)

(73) Assignee: Applera Corporation, Foster City, CA (US)

( * ) Notice: Subject to any disclaimer, the term of this patent is extended or adjusted under 35 U.S.C. 154(b) by 312 days.

(21) Appl. No.: 10/910,256

(22) Filed: Aug. 2, 2004

(65) Prior Publication Data

US 2005/0064473 A1    Mar. 24, 2005

Related U.S. Application Data

(60) Provisional application No. 60/491,270, filed on Jul. 31, 2003.

(51) Int. Cl.
*C12Q 1/68*    (2006.01)
*C07H 21/02*    (2006.01)
*C07H 21/04*    (2006.01)

(52) U.S. Cl. ................. 435/6; 536/23.1; 536/24.3
(58) Field of Classification Search ............. 435/6; 536/23.1, 24.3
See application file for complete search history.

(56) References Cited

U.S. PATENT DOCUMENTS

| | | | |
|---|---|---|---|
| 5,066,377 A | 11/1991 | Rosenbaum et al. |
| 5,068,176 A | 11/1991 | Vijg et al. |
| 5,734,058 A | 3/1998 | Lee |
| 5,736,025 A | 4/1998 | Smith et al. |
| 5,795,720 A | 8/1998 | Henco et al. |
| 5,871,908 A | 2/1999 | Henco et al. |
| 5,935,522 A | 8/1999 | Swerdlow et al. |
| 5,998,147 A | 12/1999 | Petit et al. |
| 6,017,704 A | 1/2000 | Herman et al. |
| 6,036,831 A | 3/2000 | Bishop |
| 6,265,171 B1 | 7/2001 | Herman et al. |
| 6,265,557 B1 | 7/2001 | Diamond et al. |
| 6,398,933 B1 | 6/2002 | Scott |
| 6,475,721 B2 | 11/2002 | Kleiber et al. |
| 6,486,309 B1 | 11/2002 | Gerber et al. |
| 6,613,508 B1 | 9/2003 | Ness et al. |
| 2002/0012902 A1 | 1/2002 | Fuchs et al. |
| 2002/0042060 A1 | 4/2002 | Raees et al. |

FOREIGN PATENT DOCUMENTS

| EP | 0 329 341 | 8/1989 |
|---|---|---|
| WO | WO 91/02815 | 3/1991 |
| WO | WO 96/08715 | 3/1996 |
| WO | WO 96/24687 | 8/1996 |
| WO | WO 97/40184 | 10/1997 |
| WO | WO 01/77386 | 10/2001 |
| WO | WO 02/31199 | 4/2002 |

OTHER PUBLICATIONS

Abrams et al., "Comprehensive Detection of Single Base Changes in Human Genomic DNA Using Denaturing Gradient Gel Electrophoresis and a GC Clamp," *Genomics*, vol. 7, pp. 463-475 (1990).
Alper, Joseph, "Biotechnology: Weighing DNA for Fast Genetic Diagnosis," *Science Magazine*, vol. 279:5359, pp. 2044-2045 (1998).
Chee et al., "Accessing Genetic Information with High-Density DNA Arrays," Science Magazine, vol. 274, No. 5287, Oct. 1996, pp. 610-614 (pp. 1-13).
Gao et al., "High-Throughput Detection of Unknown Mutations by Using Multiplexed Capillary Electrocphoresis With Poly(vinylpyrrolidone) Solution", Analytical Chemistry, 72:11 pp. 2499-2506 (2000).
Gao et al., 25. High-Speed High-Throughput Mutation Detection, http://www.ornl.gov/sci/techresources/Human_Genome/publicat/00santa/25.html, Research Abstracts, 2000, DOE Human Genome Program.
Gelfi et al., "Detection of point mutations by capillary electrophoresis in liquid polymers in temporal thermal gradients," Electrophoresis, 1994, vol. 15, pp. 1506-1511.

(Continued)

*Primary Examiner*—Ethan Whisenant
(74) *Attorney, Agent, or Firm*—McQuaide, Blasko, Fleming & Faulkner, Inc.

(57) ABSTRACT

A method for determining a frequency of single nucleotide polymorphism (SNP) within genomic DNA includes providing genomic DNA of each of a plurality of different organisms. The genomic DNA of each organism includes first and second portions, e.g., first and second strands. First and second amplicons are prepared from the genomic DNA of each organism. The first amplicon corresponds to the first portion of the genomic DNA and the second amplicon corresponds to the second portion of the genomic DNA.

A plurality of duplexes is prepared from the first and second amplicons of the genomic DNA of each organism. At least some of the duplexes include a portion of one of the first amplicons and a portion of one of the second amplicons.

The duplexes are subjected to temperature gradient electrophoresis to obtain first electrophoresis data indicative of the rate of SNP at a first location in the genomic DNA of the plurality of organisms.

25 Claims, 9 Drawing Sheets

OTHER PUBLICATIONS

Germer et al., "High-Throughput SNP Allele-Frequency Determination in Pooled DNA Samples by Kinetic PCR", *Genome Research*, 10:258-266 (2000).

Henco et al., "Quantitative PCR: the determination of template copy numbers by temperature gradient gel electrophoresis (TGGE)," Nucleic Acids Research, vol. 18, No. 22, pp. 6733-6734.

Hoogendoorn, et al., "Cheap, accurate and rapid allele frequency estimation of single nucleotide polymorphisms by primer extension and DHPLC in DNA pools", *Hum Genet*, 107:488-493 (2000).

Igloi, Gabor L., "Automated Detection of Point Mutations by Electrophoresis in Peptide-Nucleic Acid-Containing Gels", *BioTechniques*, 27:798-808 (1999).

Ke et al., "Selecting DNA fragments for mutation detection by temperature gradient gel electrophoresis: Application to the p53 gene cDNA," Electrophoresis, 1993, vol. 14, pp. 561-565.

Khrapko et al., "Constant denaturant capillary electrophoresis (CDCE): a high resolution approach to mutational analysis," Nucleic Acids Research, 1994, vol. 22, No. 3, pp. 364-369.

Mohlke et al., "High-throughput screening for evidence of association by using mass spectrometry genotyping on DNA pools", *PNAS*, vol. 99, No. 26, pp. 16928-16933 (2002).

Myers et al., "Detection of single base substitutions in total genomic DNA," Nature, Feb. 1985, vol. 313, p9. 495-498.

Neve et al., "Short Technical Report: Rapid SNP Allele Frequency Determination in Genomic DNA Pools by Pyrosequencing™", *BioTechniques*, vol. 32, No. 5, pp. 1138-1142 (2002).

Norton et al., "Universal, robust, highly quantitative SNP allele frequency measurement in DNA pools", *Hum Genet*, 110:471-478 (2002).

Ray et al., "Peptide nucleic acid (PNA): its medical and biotechnical applications and promise for the future", *Department of Physical Chemistry, Chalmers University of Technology*, S 412 96, Gothenburg, Sweden, pp. 1041-1060.

Riesner et al., "Temperature-gradient gel electrophoresis of nucleic acids: Analysis of conformational transitions, sequence variations, and protein-nucleic acid interactions," Electrophoresis, 1989, vol. 10, pp. 377-389.

Riesner et al., "Temperature-gradient gel electrophoresis for the detection of polymorphic DNA and for quantitative polymerase chain reaction," Electrophoresis, 1992, vol. 13, pp. 632-636.

Sasaki et al., "Precise Estimation of Allele Frequencies of Single-Nucleotide Polymorphisms by a Quantitative SSCP Analysis of Pooled DNA", *Am. J. Hum. Genet.*, 68:214-218 (2001).

Schell et al., "Detection of point mutations by capillary electrophoresis with temporal temperature gradients," Electrophoresis, 1999, vol. 20, pp. 2864-2869.

Sidransky, David, "Nucleic Acid-Based Methods for the Detection of Cancer," Science, vol. 278, Nov. 7, 1997, www.sciencemag.org, pp. 1054-1058.

Taylor et al., "Detection of Mutations and Polymorphisms on the WAVE™ DNA Fragment Analysis System," TRANSGENOMIC, Application Note 101.

Wang, David G., "Large-Scale Inditification, Mapping, and Genotyping of Single-Nucleotide Polymorphisms in the Human Genome," Science, vol. 280, May 15, 1998, pp. 1077-1082.

Wartell et al., "Detecting single base substitutions, mismatches and bulges in DNA by temperature gradient gel electrophoresis and related methods", Journal of Chromatography, pp. 169-185 (1998).

Wiese et al., "Scanning for mutations in the human prion protein open reading frame by temporal temperature gradient gel electrophoresis", Electrophoresis, pp. 1851-1860 (1995).

Zhou et al., "Quantitative detection of single nucleotide polymorphisms for a pooled sample by a bioluminometric assay coupled with modified primer extension reactions (BAMPER)", *Nucleic Acids Research*, vol. 29, No. 19 e93, pp. 1-11 (2001).

Entries for "Peltier Effect", "thermoelectric heating", "thermoelectric cooling" and "thermoelectric cooler" in the McGraw-Hill Encyclopedia of Science & Technology Online. Downloaded on Jun. 6, 2005.

"High-Throughput Detection of Unknown Mutations By Using Multiplexed Capillary Electrophoresis With Polyvinylpyrrolidone Solution", The Ames Laboratory, U.S. Department of Energy by Iowa State University, pp. 1-28.

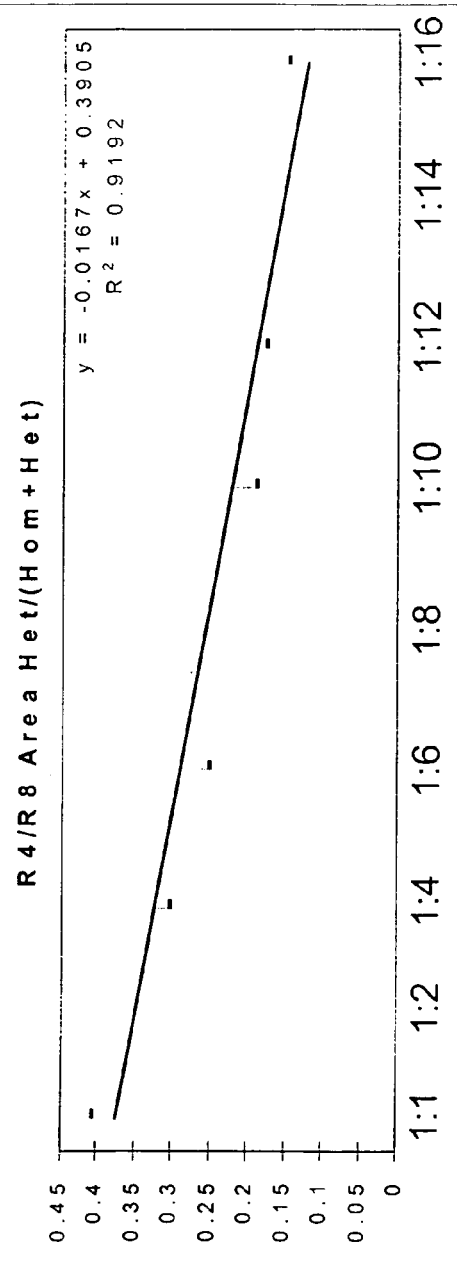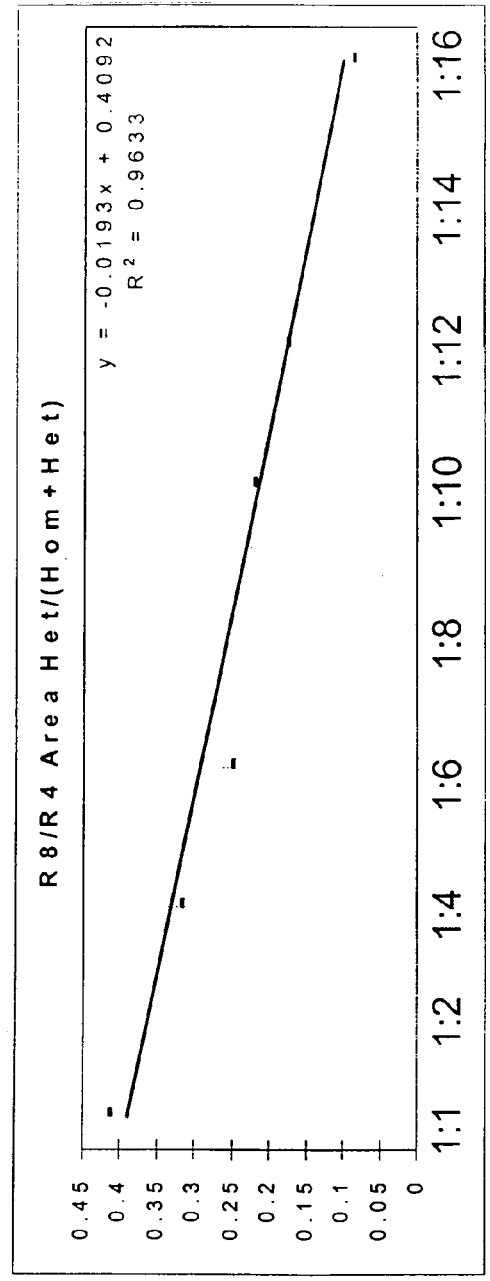
Fig 4

DETERMINATION OF SNP ALLELIC FREQUENCIES USING TEMPERATURE GRADIENT ELECTROPHORESIS

RELATED APPLICATIONS

The present application claims the benefit of U.S. provisional application No. 60/491,270, filed Jul. 31, 2003, which application is incorporated by reference herein.

FIELD OF THE INVENTION

The present invention relates to methods for determining allelic frequencies of polymorphisms, e.g., single nucleotide polymorphisms (SNP's) in genomic DNA.

BACKGROUND

A method to accurately determine SNP allelic frequencies from pooled DNA samples would greatly increase the throughput and, therefore, reduce the cost of SNP frequency determination. Such a method would also provide a reliable approach for selecting appropriate SNP's from databases for study. For example, databases of human SNPs comprise millions of SNP sites. Choosing low frequencies SNPs for a disease association study would require that a larger number of individual organisms be genotyped in order to obtain the statistically meaningful data. It has been suggested that SNPs for such studies should have a minimum allelic frequency of at least 10%. Techniques for allelic frequency determination are known.

SUMMARY

One aspect of the present invention relates to a method for determining a frequency of insertion deletions and single nucleotide polymorphism (SNP) within genomic DNA. In one embodiment, the invention comprises providing genomic DNA of each of a plurality of different organisms. Typically, the different organisms are of the same type, e.g., of the same species. The organisms may be different humans. Genomic DNA of at least some and preferably each organism preferably comprises first and second portions.

The method may comprise preparing, e.g., from the genomic DNA of each organism, first and second amplicons. For at least some and preferably for each organism the first amplicon may correspond to the first portion of the genomic DNA. For at least some and preferably for each organism the second amplicon may correspond to the second portion of the genomic DNA.

A plurality of duplexes may be prepared, e.g., from the first and second amplicons of the genomic DNA of at least some and preferably each organism. At least some of the duplexes may comprise a portion of one of the first amplicons and a portion of one of the second amplicons.

The duplexes may be subjected to temperature gradient electrophoresis to obtain first electrophoresis data indicative of the rate of SNP at the first location in the genomic DNA of the plurality of organisms.

The first portion of the genomic DNA may correspond to a portion of a first copy of a gene of the organism. Alternatively or additionally, the second portion of the genomic DNA may correspond to a portion of a second copy of the gene of the organism. For at least some and preferably for each organism, at least some of the first amplicons may comprise at least one portion corresponding to the first portion of the genomic DNA. For at least some and prefer-ably for each organism, at least some of the second amplicons may also comprise at least one portion corresponding to the second portion of the genomic DNA. The first amplicon may comprise first and second complementary polynucleotide strands. The first and second polynucleotide strands may correspond to complementary portions of the first portion of the genomic DNA. The second amplicon may comprise first and second complementary polynucleotide strands. The first and second polynucleotide strands of the second amplicon may correspond to complementary portions of the second portion of the genomic DNA.

The plurality of organisms may comprise one or more mammals. For example, at least some or all of the organisms may be humans. The plurality of organisms may comprise one or more plants. The plurality of organisms may comprise one or more fungi. The plurality of organisms may comprise one or more microbes, for example, bacteria. The organisms may be different members of the same species of organism.

The method may comprise forming a mixture comprising genomic DNA of the plurality of organisms.

Preparing the plurality of duplexes may comprise denaturing the first and second amplicons, if not previously denatured, and annealing the denatured first and second amplicons of each organism. The first and second amplicons of respective organisms are preferably annealed concomitantly, e.g., in the presence of one another. The respective first and second amplicons of some or all of the organisms may be annealed concomitantly. In one embodiment, a mixture comprising first and second amplicons of the genomic DNA of at least 2, of at least 20% of the organisms, or all of the organisms may be prepared prior to concomitantly annealing the amplicons.

The method may comprise preparing a mixture comprising genomic DNA of at least 2, of at least 20% of the organisms, or all of the organisms. The mixture may be prepared prior to the step of preparing, from the genomic DNA, first and second amplicons.

The first and second amplicons may be prepared using one or more polymerase chain reactions. One or more mutiplexed polymerase chain reactions may be used.

The method may comprise determining the rate of SNP in the genomic DNA of the plurality of organisms, the step of determining comprising using the first electrophoresis data.

The step of determining may comprise comparing the first electrophoresis data with second electrophoresis data obtained from temperature electrophoresis of a control sample. The control sample may comprise one or more control polynucleotides, preferably having at least a first genotype. The genotype of the one or more control polynucleotides may be known. One or more control polynucleotides may be heterozygous. Calibration data may be prepared, such as by subjecting one or more control polynucleotides to temperature gradient electrophoresis.

The step of determining may comprise determining a value indicative of the number of duplexes comprising a mismatch. A second value indicative of a number of duplexes not comprising a mismatch may be determined. Determining the value indicative of the number of duplexes comprising a mismatch may comprise determining at least one of: a number of one or more peaks present within a portion of the first electrophoresis data, an area of one or more peaks present within a portion of the first electrophoresis data, and an intensity of one or more peaks present within a portion of the first electrophoresis data.

The method may comprise preparing at least a first mixture comprising the first and second amplicons of the genomic DNA of each of at least some of the plurality of organisms. The mixture may be subjected to temperature gradient electrophoresis during the subjecting step.

The step of subjecting the duplexes to temperature gradient electrophoresis may comprise an injection step wherein the first and second amplicons are introduced to a separation lane and an electrophoresis step and further wherein the step of preparing the mixture is performed prior to the step of injection.

The step of subjecting the duplexes temperature gradient electrophoresis may comprise simultaneously subjecting at least 5, at least 10, at least 20, for example, at least 40 duplexes to temperature gradient electrophoresis along the same separation lane.

The method advantageously allows determination of unknown SNP's and an estimate of the allelic frequency for a pooling sample. The determination can be performed simultaneously.

DESCRIPTION OF THE DRAWINGS

FIGS. 3-7 illustrate linear relationships of peak ratios obtained from temperature gradient electrophoresis of pooled samples.

DETAILED DESCRIPTION

A method of determining SNP frequencies in pooling samples includes subjecting the samples to temperature gradient electrophoresis (TGE). A plurality of samples of genomic DNA is provided. Each sample of genomic DNA is typically from a different organism, for example, from different humans, rats, mice, pigs, or other mammal. The organisms may also be plants. For example, the genomic DNA can be obtained from seeds.

For each sample, a wild-type (WT) homozygote is mixed with a SNP homozygote at different ratios. Temperature gradient electrophoresis data indicative of the presence of heteroduplex sample components is obtained. The relationship of the peak area of heteroduplex components and the percentage of heteroduplex components in the sample is estimated using, for example, linear regression. Based on these relationships, SNP frequencies at various DNA loci of any organism of interest can be quantified. The information can be used in areas such as population genetics and disease association study.

Methods and systems for performing temperature gradient electrophoresis, determing the presence or absence of SNP's, and interpreting data generally, are disclosed in U.S. application Ser. No. 10/287,808, filed Nov. 5, 2002, which application is incorporated herein by reference in its entirety.

Figure 1:
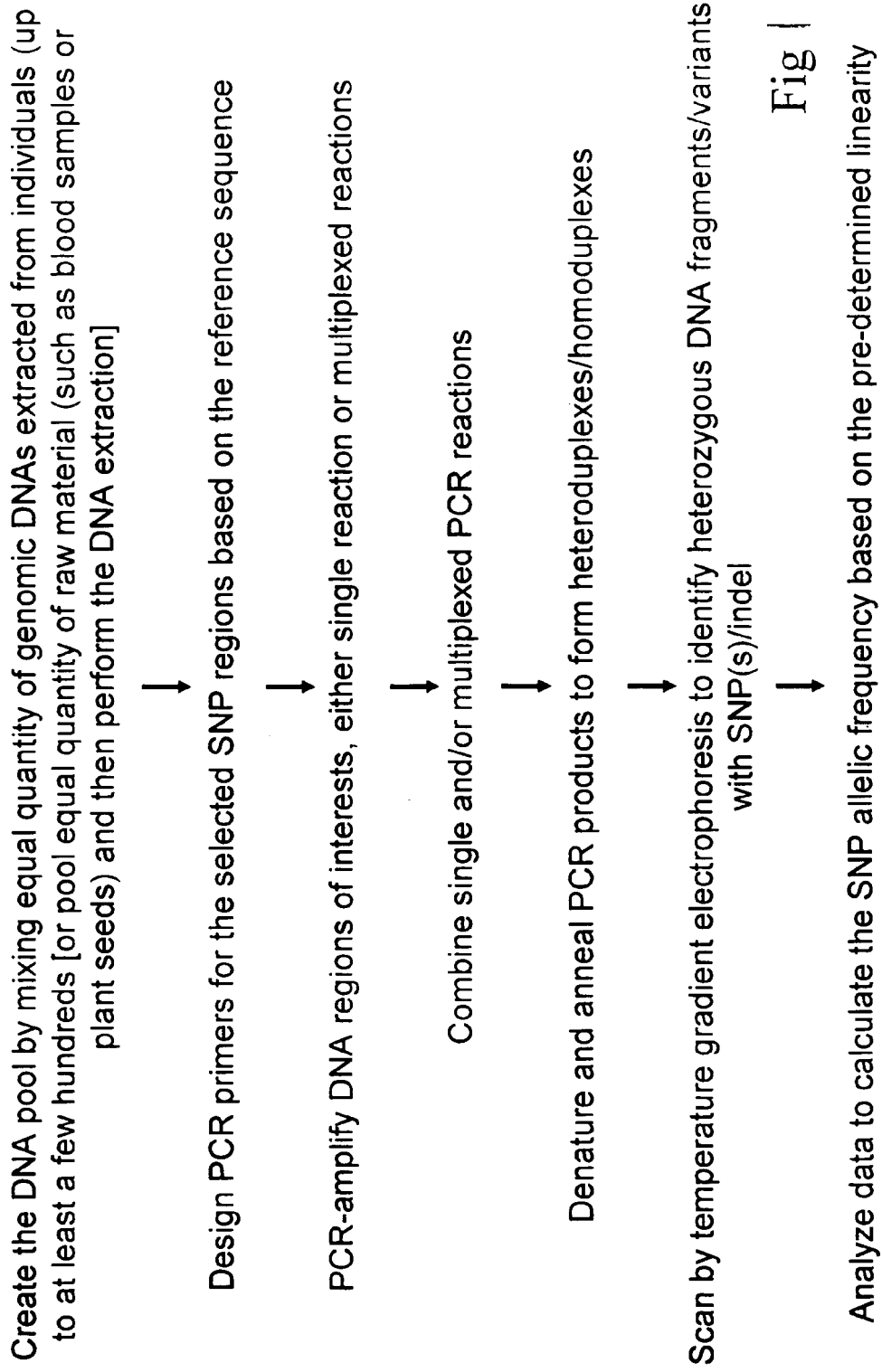
FIG. 1 is a flow chart of a method for determining SNP allelic frequencies.

Referring to FIG. 1, a method for determining SNP allelic frequency can include preparing a DNA pool by mixing quantities, e.g., equal quantities, of genomic DNA obtained from different individuals. As an alternative to pooling genomic DNA directly, quantities of biological material, e.g., tissue samples, blood samples, saliva samples, plant tissue, seeds, can be combined and genomic DNA obtained (e.g., extracted) from the combined biological material. Genomic DNA or biological material from at least 10, at least 50, at least 100, or at least 250 individuals can be pooled.

PCR primers are designed for one or more SNP regions of interest. For example, the primers can be designed based on a reference sequence. Amplification of the regions of interests can be conducted by, e.g., single reaction or multiplexed PCR. For example, PCR samples can be multiplexed based on the different sizes of amplicons from individual PCR reactions.

The amplicons are then denatured and annealed to form two homoduplexes of original DNA molecules, and two heteroduplexes each with a mismatch at the SNP site. The denaturing and annealing is typically performed at a rate slow enough that a substantial fraction of originally paired DNA single strands pair with other strands upon annealing.

Figure 2:
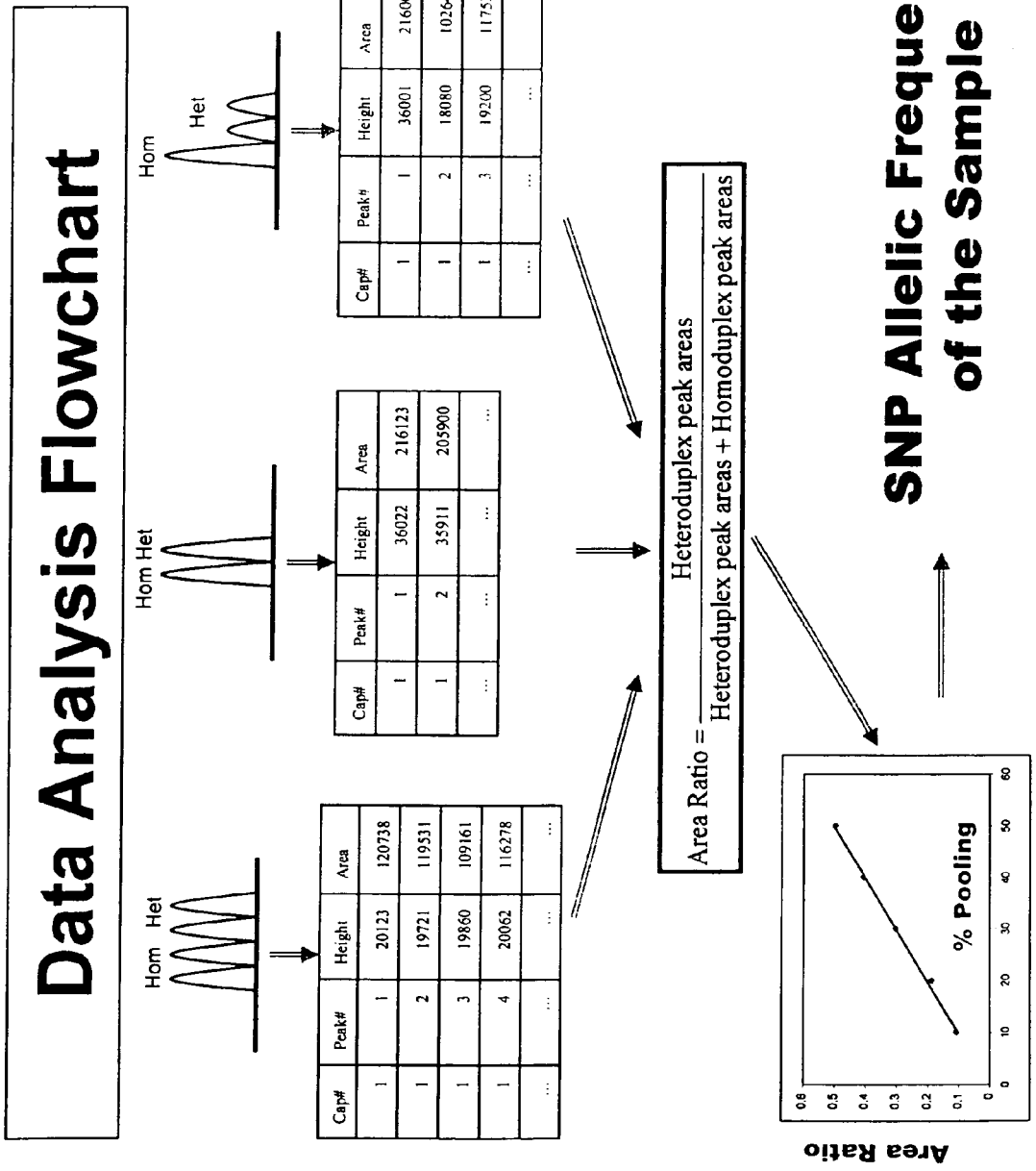
FIG. 2 is a data analysis flowchart illustrating exemplary aspects of the method of the flowchart of FIG. 1.
Figure 2:
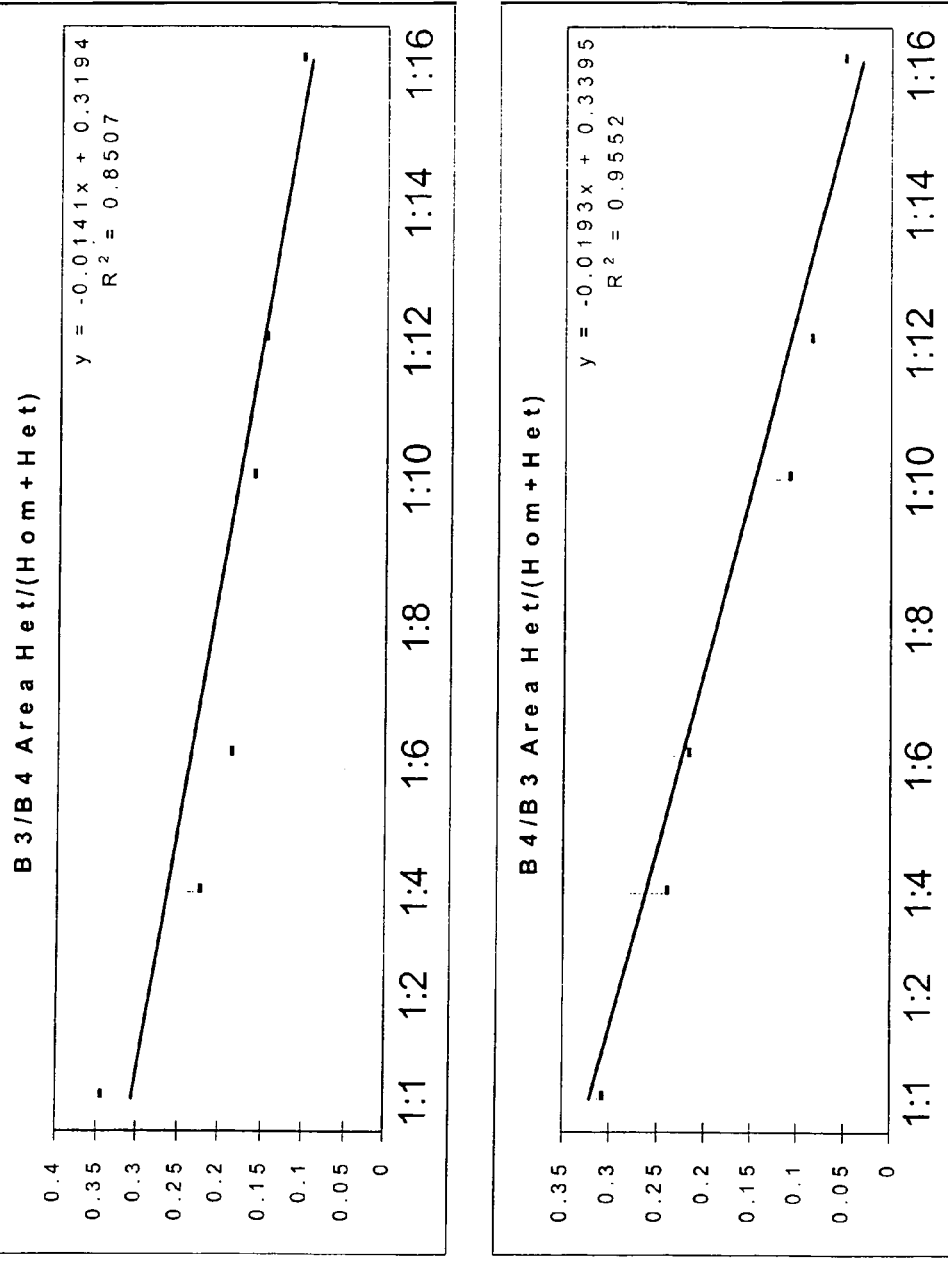

Referring to FIG. 2, the amplicons are subjected to temperature gradient electrophoresis, e.g., temperature gradient capillary electrophoresis, to differentiate the homoduplexes and heteroduplexes. Strands annealed to form The SNP frequency may be obtained by, for example, comparing the peak-area ratio of [heteroduplex peak areas/(heteroduplex peak areas+homoduplex areas)] with the pre-determined linear relationship (FIGS. 1 and 2). It should be noted that the content of steps, number of steps and ordering of steps in FIGS. 1 and 2 are exemplary, not mandatory.

One embodiment of the present invention comprises separating duplexes derived from genomic DNA of various organisms from one another along the same separation lane. This method provides a universal linearity for any amplicon containing a SNP site of interest. This is effective at least because all four species of molecules have an equal proportion (1:1:1:1) in a typical 1:1 mixture of WT homozygote with SNP homozygote, while the peak area of heteroduplex components is generally directly proportional to the percentage of SNP homozygote in a pooling sample. This embodiment provides a procedure useful in detecting unknown SNPs and accurately estimating their frequencies in pooling samples simultaneously. This embodiment may include use of separation gel matrices with increased resolution, a pair of GC-clamped primers, and prediction of TGE temperature ranges having narrower temperature gradients.

If the estimation accuracy is only loosely required (for example, one may just want to select SNPs with frequencies ranging from 20-40%) the method also has the potential to be used for detecting unknown SNPs and calculating the frequency simultaneously since the detection tends to lose its sensitivity below the 10% level. Thus, using the SpectruMedix's 24-, 96-, 192- or 384-capillary instrument, SNP frequencies of various DNA loci of any organism of interest can be quantitated in an extremely highthroughput matter in areas such as population genetics and disease association studies.

EXAMPLES

The following non-limiting examples relate to methods of using temperature gradient elecctrophoresis (TGE) to determine SNP frequencies in pooling samples.

Five samples of genomic DNA were tested in this study. For each sample, the wild-type (WT) homozygote was mixed with the SNP homozygote at different ratios. Electrophoresis data indicative of the presence of heteroduplex sample components was obtained. The relationship of the peak area of heteroduplex components and the percentage of heteroduplex components in the sample may be estimated using, for example, linear regression. Different methods of estimation were used to obtain a best fitting curve. The results showed that a linear relationship with a high R2 value may be achieved, which indicates that SNP frequencies of various DNA loci of any organism of interest can be quantified in an extremely high-throughput matter in areas such as population genetics and disease association study.

Five samples (A, B, H, R4/6 and R4/8) with different SNP's were obtained. The DNA ranged in size from 200 to 650 bp. Heterozygous samples or pools were generated by mixing the WT homozygote with the SNP homozygote at ratios ("pooling ratios") of 1:0, 1:1 and 20:1. The relative concentration of WT and SNP homozygotes was estimated by running samples on agarose gel and in capillary electrophoresis, and comparing the peaks obtained with those obtained from a molecular ladder.

Figure 5:
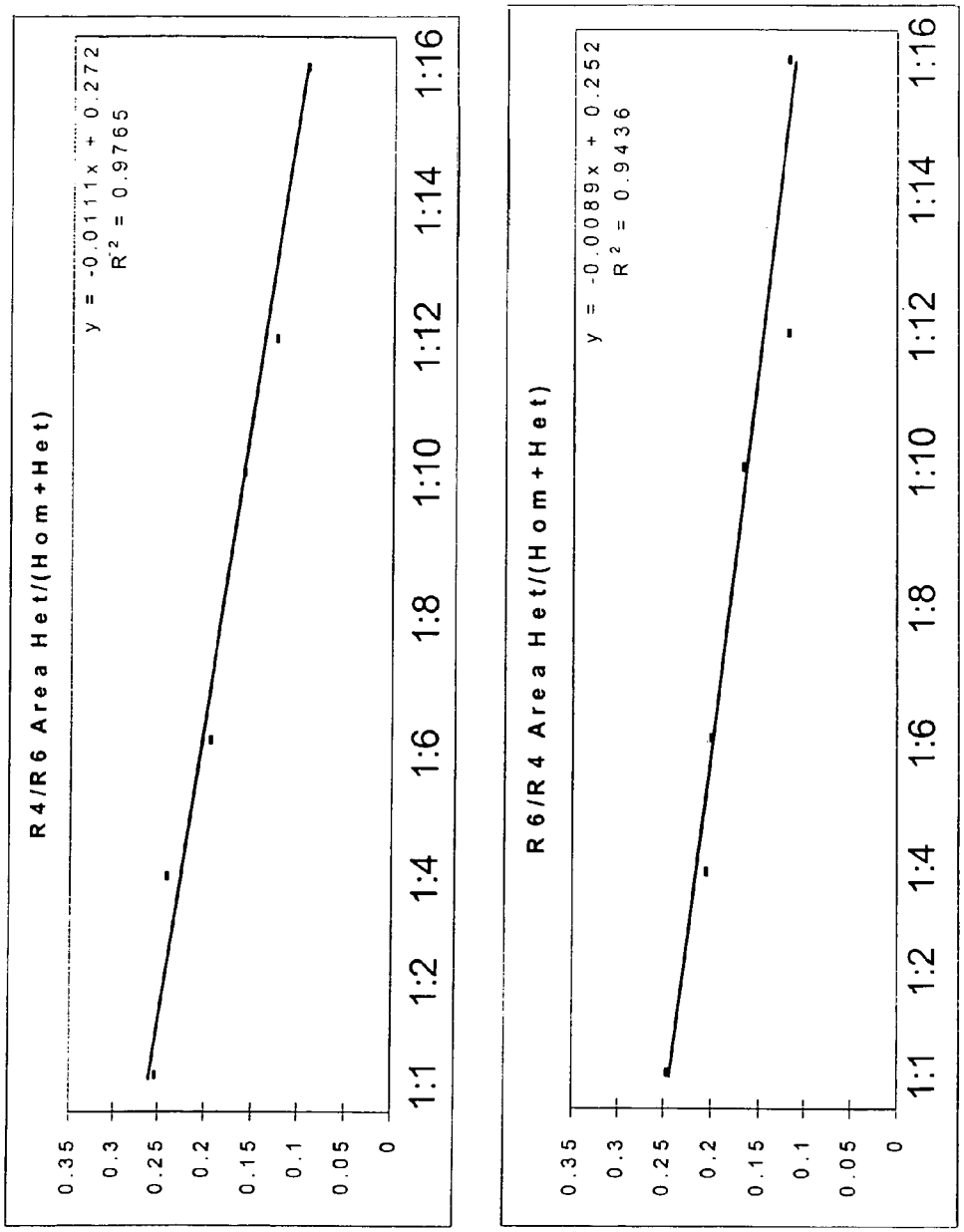

In order to verify the accuracy of the concentration estimation, reciprocal samples were also created by mixing the SNP homozygote with the WT homozygote at ratios from 1:0, 1:1 to 20:1 for three of the five samples. In all these three cases, a highly similar linear relationship was found between peak areas and the pooling ratios (FIGS. 3-5). Similar results were obtained for different injection conditions indicating the robustness of the method.

All samples were placed in a single plate and subjected to temperature gradient capillary electrophoresis using a SpectruMedix Reveal capillary electrophoresis instrument. In addition to testing different injection conditions, analyses were performed with different temperature gradients. Electrophoresis data obtained using a temperature ramp of from 50° C.-60° C. were analyzed using ChemSpectrum software to generate a peak table including peak parameters including peak area, peak height, and the like (FIG. 2). The output was then exported to the Excel program and testing of different methods of calculation and curve fitting were performed with this software.

Three methods for estimating the allelic frequencies were studied: (1) linearity between peak areas of heteroduplex components and the pooling ratio percentage, (2) linearity between the ratio of heteroduplex peak areas to the homoduplex areas and the pooling ratio percentage, and (3) linearity between (i) the ratio of heteroduplex peak areas and the sum of the heteroduplex peak areas and the homoduplex peak areas and (ii) the pooling ratio percentage. The highest value of R2 (correlation coefficient) was used to select the best fitting curve for linearity.

Three methods of establishing a relationship between signal intensity of mutant components and the percentage of mutant in a pooling sample were tested: 1) linearity between peak areas of heteroduplex components and the percentage of pooling, 2) linearity between the ratio of [heteroduplex peak areas/homoduplex areas] and the percentage of pooling and 3) linearity between the ratio of [heteroduplex peak areas/(heteroduplex peak areas+homoduplex areas)] and the percentage of pooling. We found that the third method usually generated the best fitting linear curve with the highest value of R2 (correlation coefficient).

The results (FIGS. 3-7) indicated that the TGCE method could be applied for quantitation of SNP allelic frequencies ranging from 10 to 50%. Different amplicons may produce different relationships. In one embodiment, the relationship may be determined for different amplicons corresponding to regions of DNA having or suspected of having a SNP.

As a result, every amplicon containing a SNP may require a pre-determined linearity. The linearity was proven between the ratio of [heteroduplex peak areas/(heteroduplex peak areas+homoduplex areas)] and the percentage of pooling for quantitation of SNP allelic frequencies ranging tom 10 to 50%. The method can be applied for estimation of SNP frequencies by a multiplexed capillary array in a high throughput matter in areas such as population genetics and disease association study.

Figure 9:
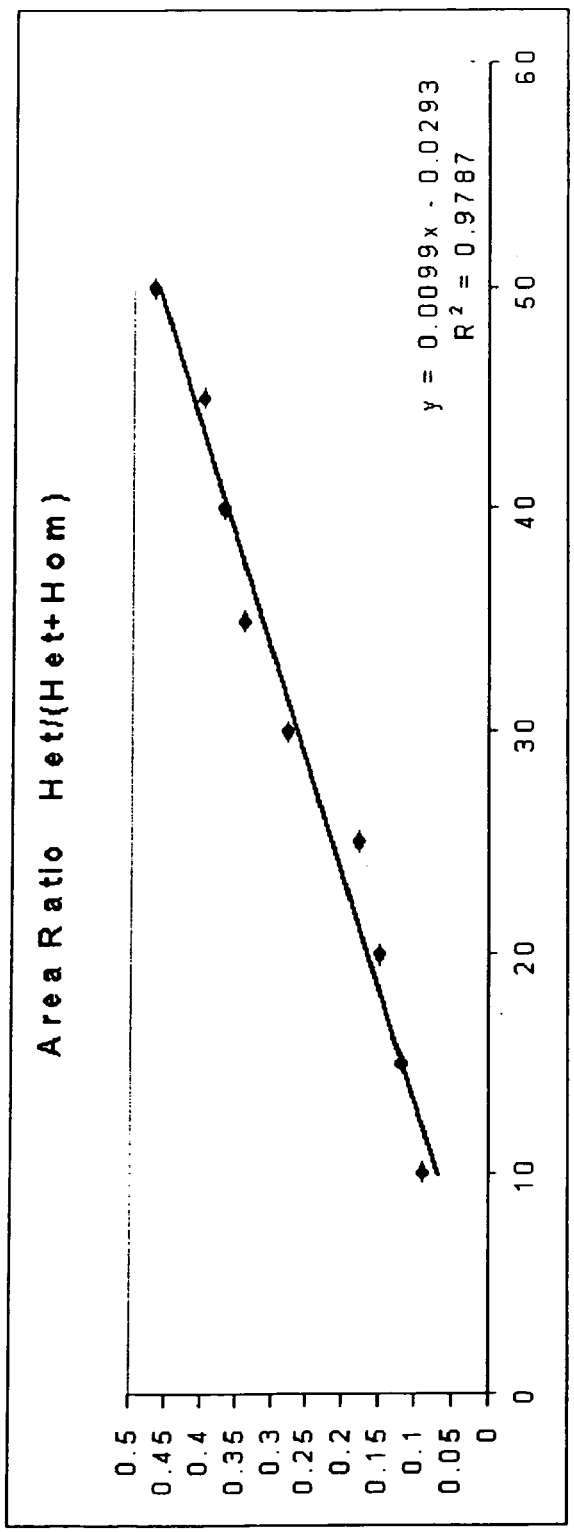
FIGS. 8 and 9 illustrate peak shapes obtained for various ratios of control and sample amplicons subjected to temperature gradient electrophoresis.
Figure 7:
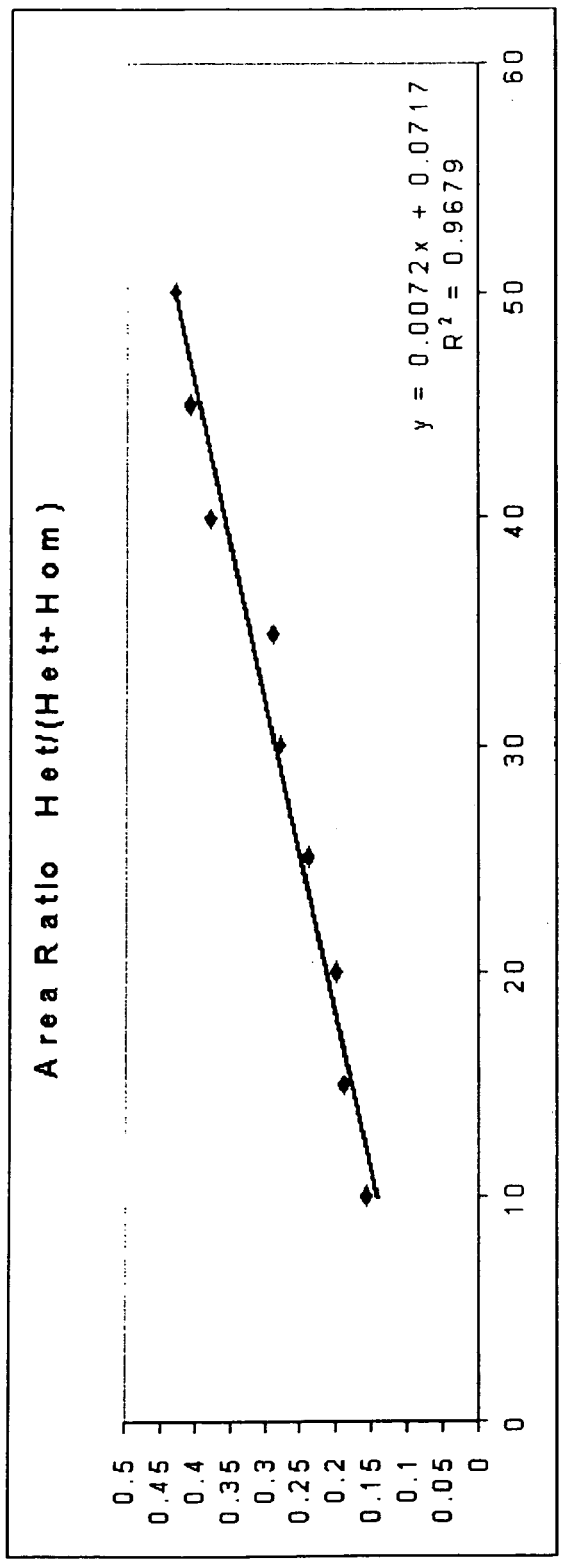
Figure 8:
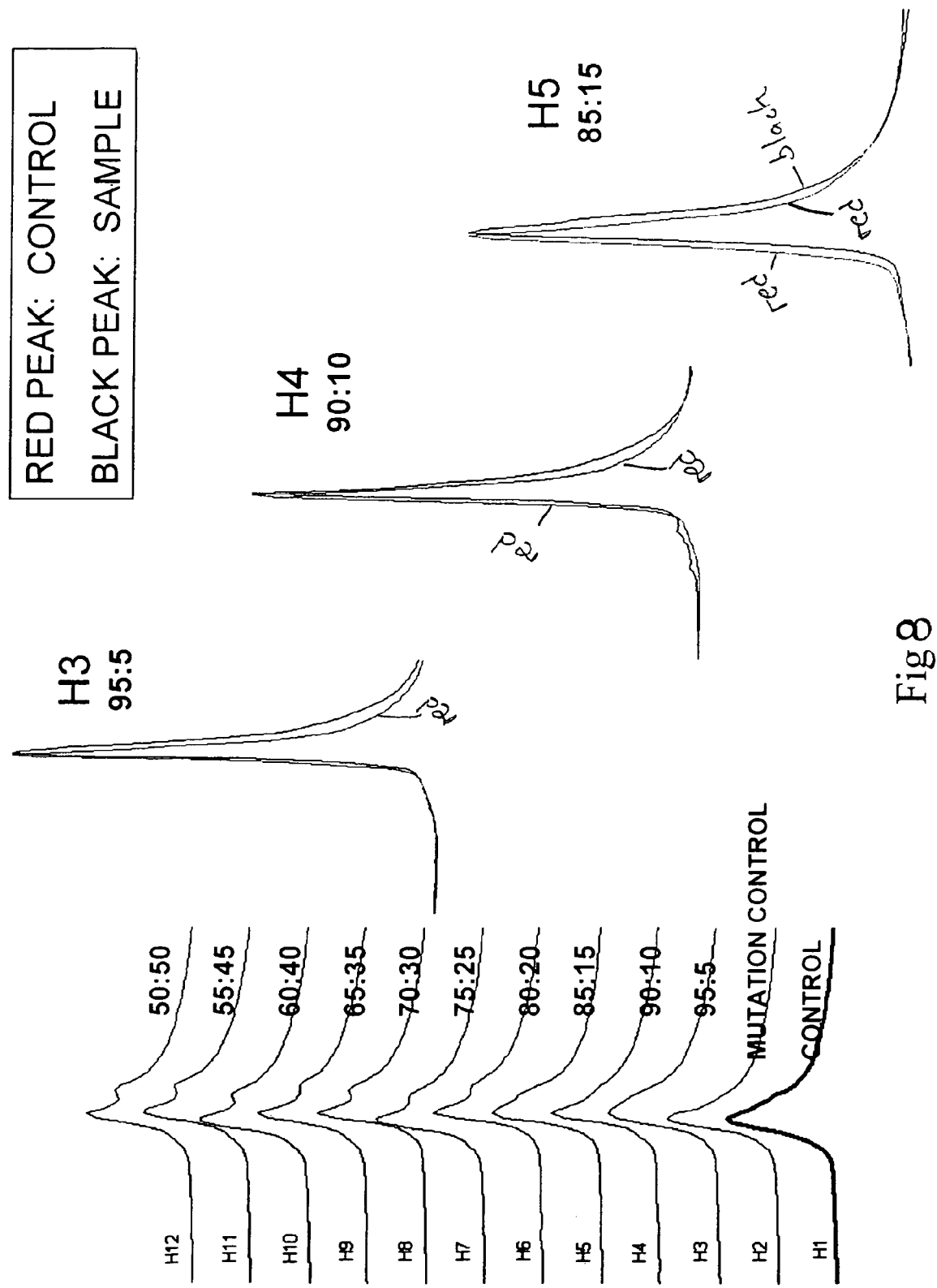
Figure 9:
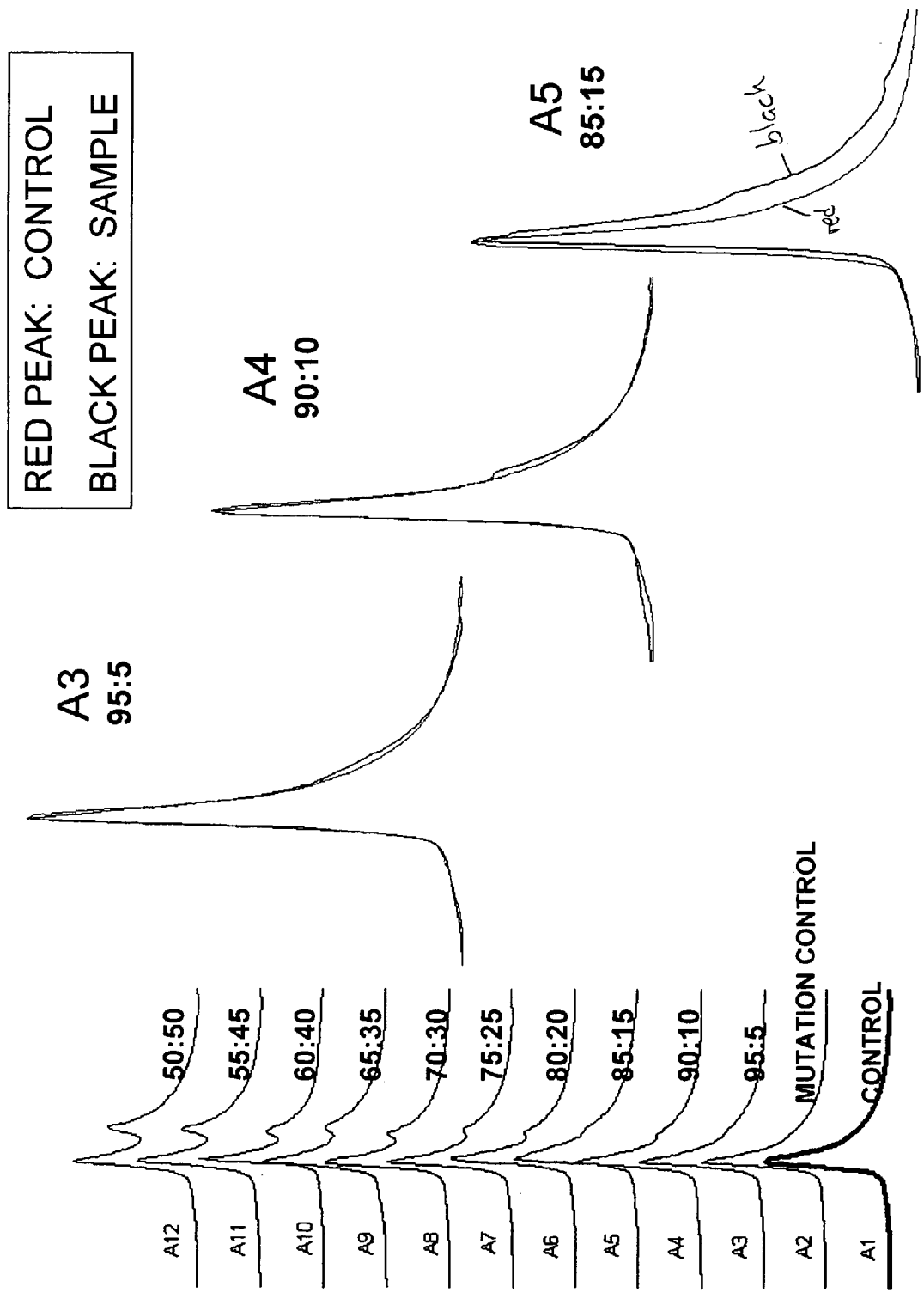

Referring to FIGS. 8 and 9, the variation in peak area of heteroduplex components and the percentage of heteroduplex components is demonstrated using different ratios of control and mutation control genomic DNA samples.

The following references, which are not admitted as prior art, are incorporated herein. Copies of the references are attached. Soren Germer, Michael J. Holland, and Russell Higuchi, "HighThroughput SNP Allele-Frequency Determination in Pooled DNA Samples by Kinetic PCR", Genome Res. 2000 10: 258-266. Guo-hua Zhou, Masao Kamahori, Kazunori Okano, Gao Chuan, Kunio Harada and Hideki Kambara, "Quantitative detection of single nucleotide polymorphisms for a pooled sample by a bioluminometric assay coupled with modified primer extension reactions (BAMPER)", Nuceic Acids Research, 2001, Vol. 29, No. 19 e93. Tomonari Sasaki, Tomoko Tahira, Akari Suzuki, Koichiro Higasa, Yoji Kukita, Shingo Baba, and Kenshi Hayashi, "Precise Estimation of Allele Frequencies of Single-Nucleotide Polymorphisms by a Quantitative SSCP Analysis of Pooled DNA", Am. J. Hum. Genet. 68:214-218, 2001. Nadine Nortin, Nigel M. Williams, Hywel J. Williams, Gillian Spurlock, George Kirov, Derek W. Morris, Bastiaan Hoogendoorn, Michael J. Owen, Michael C. O'Donovan, "Universal, robust, highly quantitative SNP allele frequency measurement in DNA pools", Hum Genet (2002) 110:471-478. Bastiaan Hoogendoorn, Nadine Norton, George Kirov, Nigel Williams, Marian L. Hamshere, Gillian Spurlock, Jehannine Austin, Mark K. Stephens, Paul R. Buckland, Michael J. Owen, Michael C. O'Donovan, "Cheap, accurate and rapid allele frequency estimation of single nucleotide polymorphisms by primer extension and DHPLC in DNA pools", Hum Genet (2000) 107: 488-493. B. Neve, P. Froguel, L. Corset, E. Vaillant, V. Vatin, and P. Boutin, "Rapid SNP Allele Frequency Determination in Genomic DNA Pools by Pyrosequencing", BioTechniques 32:1138-1142 (May 2002). Karen L. Mohlke, Michael R. Erdos, Laura J. Scott, Tasha E. Fingerlin, Anne U. Jackson, Kaisa Silander, Pablo Hollstein, Michael Boehnke, and Francis S. Collins, "High-throughput screening for evidence of association by using mass spectrometry genotyping on DNA pools", PNAS dec. 24, 2002, Vol. 99, No. 26.

What is claimed is:

1. A method for determining a rate of single nucleotide polymorphism (SNP) at a first location genomic DNA of a plurality of organisms, comprising:
   providing genomic DNA of each of a plurality of different organisms, the genomic DNA of each organism comprising first and second portions;
   preparing, from the genomic DNA of each organism, first and second amplicons, for each organism (i) the first amplicon corresponding to the first portion of the genomic DNA and (ii) the second amplicon corresponding to the second portion of the genomic DNA;
   preparing, from the first and second amplicons of the genomic DNA of each organism, a plurality of duplexes, at least some of the duplexes comprising (i) a portion of one of the first amplicons and (ii) a portion of one of the second amplicons; and
   subjecting the duplexes to temperature gradient electrophoresis to obtain first electrophoresis data indicative of the rate of SNP at the first location in the genomic DNA of the plurality of organisms.

2. The method of claim 1, wherein, for each organism, the first portion of the genomic DNA corresponds to a first copy of a first portion of a gene of the organism and the second portion of the genomic DNA corresponds to a second copy of the first portion of the gene of the organism.

3. The method of claim 2, wherein, for each organism, the first amplicon comprises at least one portion corresponding to the first portion of the genomic DNA and the second amplicon comprises at least one portion corresponding to the second portion of the genomic DNA.

4. The method of claim 3, wherein, for each organism, the first amplicon comprises first and second complementary polynucleotide strands, the first and second polynucleotide strands corresponding to complementary portions of the first portion of the genomic DNA.

5. The method of claim 3, wherein, for each organism, the second amplicon comprises first and second complementary polynucleotide strands, the first and second polynucleotide strands corresponding complementary portions of the second portion of the genomic DNA.

6. The method of claim 2, wherein the organisms are mammals.

7. The method of claim 6, wherein the organisms are humans.

8. The method of claim 2, wherein the organisms are plants.

9. The method of claim 2, wherein the organism are microbes.

10. The method of claim 1, wherein, for at least some of the organisms, preparing the plurality of duplexes comprises:
    providing the first and second amplicons in denatured form; and concomitantly annealing the denatured first and second amplicons of each organism.

11. The method of claim 10, comprising, prior to the step of concomitantly annealing, preparing a mixture comprising first and second amplicons of the genomic DNA of each of at least 2 of the organisms.

12. The method of claim 1, comprising preparing a mixture comprising genomic DNA of at least 2 of the organisms, prior to the step of preparing from the geromic DNA of each organism first and second amplicons.

13. The method of claim 1, further comprising determining the rate of SNP in the genomic DNA of the plurality of organisms, the step of determining comprising using the first electrophoresis data.

14. The method of claim 1, comprising a polymerase chain reaction step, prior to the step of preparing from the genomic DNA of each organism first and second amplicons.

15. The method of claim 14, wherein the polymerase chain reaction is a multiplex reaction.

16. The method of claim 13, wherein the step of determining comprises comparing the first electrophoresis data with second electrophoresis data obtained from temperature electrophoresis of a control sample comprising control polynucleotides having at least a first genotype.

17. The method of claim 16, wherein the first genotype is known.

18. The method of claim 17, wherein at least some of the control polynucleotides are heterozygous.

19. The method of claim 13, wherein the step of determining comprises determining a value indicative of the number of duplexes comprising a mismatch and a second value indicative of a number of duplexes not comprising a mismatch.

20. The method of claim 19, wherein determining the value indicative of the number of duplexes comprising a mismatch comprises determining at least one of: a number of one or more peaks present within a portion of the first electrophoresis data, an area of one or more peaks present within a portion of the first electrophoresis data, and an intensity of one or more peaks present within a portion of the first electrophoresis data.

21. The method of claim 1, comprising preparing calibration data, the calibration data prepared from temperature gradient electrophoresis of a plurality of control polynucleotides.

22. The method of claim 1, comprising preparing at least a first mixture comprising the first and second amplicons of the genomic DNA of each of at least some of the plurality of organisms and wherein the step of subjecting comprises subjecting the mixture to TGE.

23. The method of claim 22, wherein the step of subjecting the duplexes to temperature gradient electrophoresis comprises an injection step wherein the first and second amplicons are introduced to a separation lane and an electrophoresis step and further wherein the step of preparing the mixture is performed prior to the step of injection.

24. The method of claim 1, wherein the different organisms are different members of the same species of organism.

25. The method of claim 1, comprising forming a mixture comprising genomic DNA of the plurality of organisms.

* * * * *